United States Patent
Carley et al.

(10) Patent No.: US 7,211,101 B2
(45) Date of Patent: May 1, 2007

(54) METHODS FOR MANUFACTURING A CLIP AND CLIP

(75) Inventors: Michael T. Carley, San Jose, CA (US); Richard S. Ginn, San Jose, CA (US)

(73) Assignee: Abbott Vascular Devices, Abbott Park, IL (US)

( * ) Notice: Subject to any disclaimer, the term of this patent is extended or adjusted under 35 U.S.C. 154(b) by 409 days.

(21) Appl. No.: 10/335,075

(22) Filed: Dec. 31, 2002

(65) Prior Publication Data

US 2004/0039414 A1 Feb. 26, 2004

Related U.S. Application Data

(63) Continuation-in-part of application No. 10/081,726, filed on Feb. 21, 2002, now Pat. No. 6,623,510, and a continuation-in-part of application No. 09/732,178, filed on Dec. 7, 2000, now Pat. No. 6,719,777.

(51) Int. Cl.
*A61B 17/08* (2006.01)
*A61B 17/00* (2006.01)

(52) U.S. Cl. .................................................. 606/213

(58) Field of Classification Search ............. 606/213, 606/216, 217, 219, 220, 221, 151, 153, 156
See application file for complete search history.

(56) References Cited

U.S. PATENT DOCUMENTS

| | | | |
|---|---|---|---|
| 4,665,906 | A | 5/1987 | Jervis |
| 6,623,510 | B2 | 9/2003 | Carley et al. |
| 6,276,704 | B1 | 4/2004 | Loshakove et al. |
| 2002/0082641 | A1 | 6/2002 | Ginn et al. |
| 2002/0188318 | A1 | 12/2002 | Carley et al. |

FOREIGN PATENT DOCUMENTS

FR 2 722 975 A1 2/1996

OTHER PUBLICATIONS

Berowe, A. et al., "Vascular Port Device", PCT Publication No. WO 99/62408, Dec. 9, 1999.
Lashakove, A. et al., "Vascular Closure Device", PCT Publication No. WO 00/56223, Sep. 28, 2000.
Lashakove, A., et al., "Advanced Closure Device", PCT Publication No. WO 00/56227, Sep. 28, 2000.

*Primary Examiner*—Pedro Philogene
(74) *Attorney, Agent, or Firm*—Workman Nydegger

(57) ABSTRACT

The present invention relates to a method of making clips which can be used to engage body tissue for the purpose of closing wounds. Such clips are generally annular in shape and have radially inwardly extending tines. It is often desirable for such clips to have a small lateral dimension, but manufacturing difficulty has been encountered in making small clips because of the difficulty in cutting materials accurately when attempting to produce a clip with closely packed elements. The present invention avoids these difficulties by first forming a precursor which, in one embodiment, has the tines extending radially outwardly from the annular body and then forms the clip by inverting the precursor such that the tines extend radially inwardly. In an alternate embodiment, the precursor is formed with an over-sized lateral dimension and then compressed inwardly to bring the tines closer together and to reduce the lateral dimension of the precursor. It is preferred to manufacture such clips from a superelastic alloy such as nickel-titanium, in which case the inverted or compressed precursor must be heated and quenched to heat set the clip in its final shape.

11 Claims, 5 Drawing Sheets

METHODS FOR MANUFACTURING A CLIP AND CLIP

RELATED APPLICATIONS

This application is a continuation-in-part of U.S. patent application Ser. No. 10/081,726, filed Feb. 21, 2002 now U.S. Pat. No. 6,623,510 and is a continuation-in-part of U.S. patent application Ser. No. 09/732,178, filed Dec. 7, 2000 now U.S. Pat. No. 6,719,777, the disclosures of each of which are incorporated by reference herein.

FIELD OF INVENTION

The use of certain types of clips, which are initially generally planar and which are deformed to non-planar configuration prior to use, to close openings through tissue, e.g., into body lumens, and more particularly to close a puncture made to gain access to a blood vessel or other body lumen is known. Such clips are generally annular and have tines extending radially from an annular body. For example, such clips are disclosed in the aforementioned co-pending applications and in published PCT Applications WO/99/62408, WO/00/56223 and WO/00/56227, the disclosures of which are incorporated by reference herein. Various methods, e.g., stamping, laser cutting, chemical etching and the like have been used to form the clips from a sheet of metal. Conventional manufacturing methods are limited with regard to minimizing the space between the tines because the necessary manufacturing tolerances require that sufficient space be allowed for the manufacturing tools and/or processing materials. Improved methods of manufacturing these types of clips and the clips resulting from them would make such clips more effective for many such uses.

SUMMARY OF THE INVENTION

The present invention is directed to methods for manufacturing tissue engaging clips in a manner in which a clip-precursor is first formed and such precursor is then reconfigured into the final shape of the clip. In a preferred embodiment of the invention, a clip having an annular or hoop-shaped generally planar configuration with radially inwardly extending tines is manufactured by first forming a precursor with the tines extending radially outward and then reconfigured by inserting the precursor to its final shape with the tines extending radially inward and then heat setting the clip in this configuration. This permits the tines to be packed more closely together which enhances the sealing function of the clip and reduces the size of the clip's footprint. As will be explained in more detail herein, this manufacturing method overcomes the limitations of conventional methods in which the clip is manufactured in its final configuration.

In another preferred embodiment, an annular or hoop-shaped planar clip precursor with radially inwardly extending tines is first manufactured in an oversize configuration and then has its lateral dimensions reduced to pack the tines closer together and to reduce the footprint of the clip and then heat set in that configuration.

DETAILED DESCRIPTION OF THE INVENTION

The clips manufactured according to the present invention are useful for engaging tissue so as to connect tissue segments together or to close and/or seal openings through tissue such as a puncture wound in a body lumen. These clips may be used by deforming them from their generally planar configuration such that the tines are pointing in a direction generally transverse to the plane, holding the clip in this deformed condition, deploying the clip proximal to the tissue to be engaged and removing the deforming force such that the clip engages the tissue and attempts to return to its original generally planar configuration. The methods and apparatus disclosed in the above-mentioned U.S. patent application Ser. Nos. 10/081,726 and 09/732,178 can be used to deploy the clips of the present invention to engage tissue and close or seal an opening.

In such use, the deformation of the clip causes the tines to be directed generally axially away from the body of the clip and it is the elastic property of the deformed clip which causes it to attempt to return to its original generally planar configuration. The body of the device may comprise a series of looped elements which generally define an endless zigzag pattern, e.g., a sinusoidal pattern, extending about a central access. The looped elements are believed to facilitate deforming the device between the planar and transverse configurations, e.g., by distributing stresses through the device and minimizing localized stresses in the curved regions.

Figure 1A:
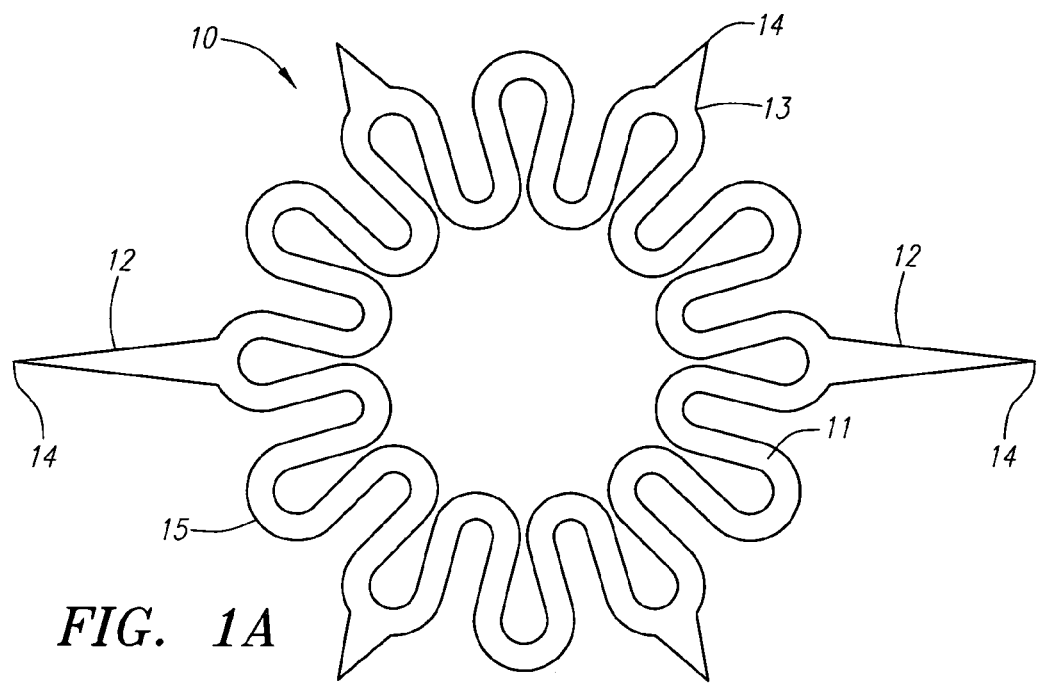
FIGS. 1A and 1B illustrate the before and after configuration of a clip manufactured according to one embodiment of this invention.

In a first preferred embodiment of the present invention, a clip precursor is first formed from a sheet of material, preferably a superelastic alloy, such as a nickel-titanium alloy ("Nitinol") alloy. The property of superelasticity and of certain alloys which possess that property is disclosed in U.S. Pat. No. 4,665,906 which is incorporated by reference herein. This forming can be done by removing portions of the material by cutting, chemical etching, laser cutting, photochemical etching, stamping, electrical discharge machining and the like to produce a precursor such as that shown in FIG. 1A which has radially outward extending tines. The precursor can then be polished using one or more processes such as electropolishing, tumbling, sand blasting, sanding and the like or such polishing can be done as a final step after the clip is formed. Forming of a precursor in this manner does not require working to tolerances as close as those which would be required if the clip was to be manufactured in its final configuration shown in FIG. 1B because the radially outwardly extending tines of the precursor shown in FIG. 1A are easily accessible by the forming tool whereas attempting to directly form the clip with radially inwardly extending tines which are closely spaced requires difficult high precision metal cutting. Thus, manufacture of a precursor which is then reconfigured to final clip shape permits the achievement of closer spacing between the elements of the final clip than would otherwise be achievable with conventional methods.

The precursor 10 comprises a hoop-shaped planar body 11 which has outwardly extending primary (longer) tines 12 and secondary (shorter) tines 13. For example, the primary trials may be 0.070 to 0.105 inches in length and the secondary tines may be 0.025 to 0.035 inches in length. Each of the tines terminates in a point 14. When the precursor 10 has been reconfigured into clip 16 shown in FIG. 1B, the tines 12 and 13 become the tissue engaging portions of the clip. The tines may be sharpened or given a shape, e.g., barbs (not shown), while the device is in the precursor state. The body 11 may compromise connecting links such as loops 15. These links may have any suitable shape provided that such shape does not interfere with inversion of the precursor 10.

The precursor 10 is then inverted to reconfigure it into the shape of clip 16. In this preferred embodiment in which the precursor is formed from a sheet of nickel-titanium alloy, the inverted precursor is then heat set, e.g., by heating to a temperature of 510° C., and then quenched to cool to room temperature. The clip 16 will now be in the austenitic state.

Heat setting and quenching are essential to successful practice of the invention with superelastic alloys. As explained in more detail in U.S. Pat. No. 4,665,906, a superelastic alloy such as nickel-titanium exists in two states, the austenitic state and the martensitic state. Such alloys will initially be in the austenitic state, e.g., when the precursor is formed. However, when the precursor is inverted to take the shape of the final clip, the stress experienced by the alloy during the inversion will cause the alloy to be partially or wholly converted to the martensitic state. Such a martensitic state is commonly referred to as stress-induced martensite. Such martensite structure has the property of superelasticity and the inverted precursor would revert to its original shape if not held in the inverted configuration.

Figure 1B:
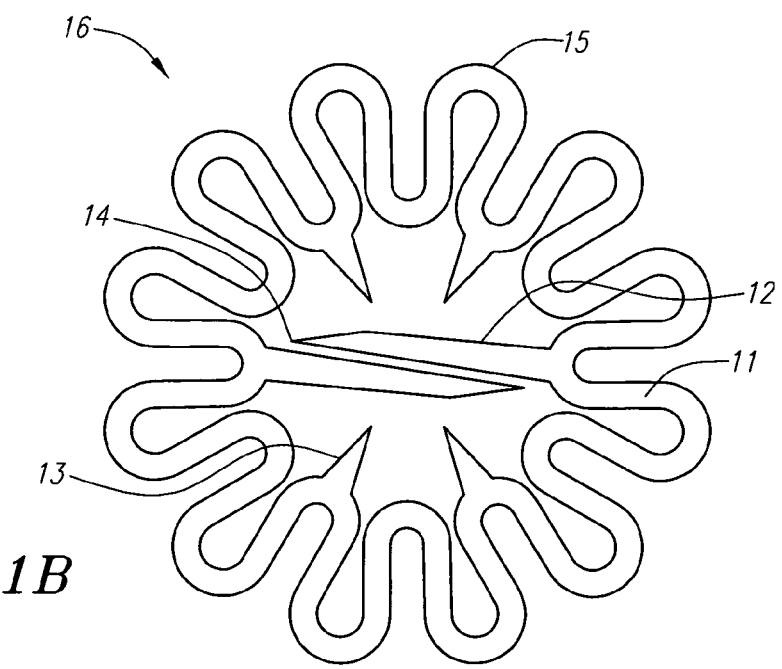

Since, if the inverted precursor was left in the martensitic state, it would want to elastically revert to its original uninverted state, it must be converted back to austenite. Thus, heating and quenching are required to convert the inverted precursor from the martensitic state to the austenitic state such that the clip is stable in its planar configuration as shown in FIG. 1B and will retain that configuration.

The times and temperatures for heat setting of superelastic alloys of various compositions can be determined from existing literature or can be determined empirically without any difficulty. The clips are small in size and the heating and quenching may be done with any conventional heating and quenching equipment. For example, once inverted, the inverted precursor can be held in that configuration and placed in a fixture which will hold it in the inverted configuration during heat setting.

Figure 4:
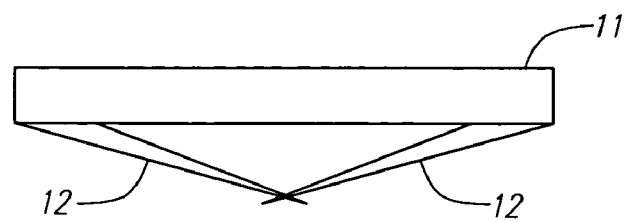
FIG. 4 illustrates a clip which, while generally planar, has tines which extend radially inwardly at an angle to the plane defined by the body.

When clips are manufactured according to the present invention, the space between the tines may actually be eliminated, i.e., after inverting the precursor, the tines may be in contact with each other, in either a side-by-side or an over-and-under relationship. The number, length and spacing of the tines may be varied according to the desires of the manufacturer. Furthermore, while use of a planar precursor is a convenience in manufacturing, a planar configuration is not required. For example, the precursor could be bent along a diameter or major or minor axis of the precursor and could be heat set in such a bent configuration. Alternatively, the clip, while generally planar, may have the tines extending at an acute angle to the plane defined by the body as shown in FIG. 4 in which the body 11 and tines 12 are shown.

Furthermore, manufacturing from a sheet of material is a convenience, but other manufacturing techniques, including joining of components such as the tines to the body, can be accomplished by welding, brazing, or other known methods of joining materials. In such cases, one or more of such components may be circular in cross-section or tubular in configuration.

Still further, the clip need not be fabricated from a single material, e.g., the tines may be manufactured from a different material than the body. In such cases, a portion of the clip such as the tines may be bioabsorbable provided that the final clip is capable of elastic recovery after being deformed. An advantage of the present invention is that it permits the production of clips with tines that are 30 to 40% or more longer than those which could be made with prior direct cutting methods, because there is no limit on the length of the tine which is formed on the precursor. Thus, after the precursor is inverted, the tines may overlap the annular body.

Figure 2A:
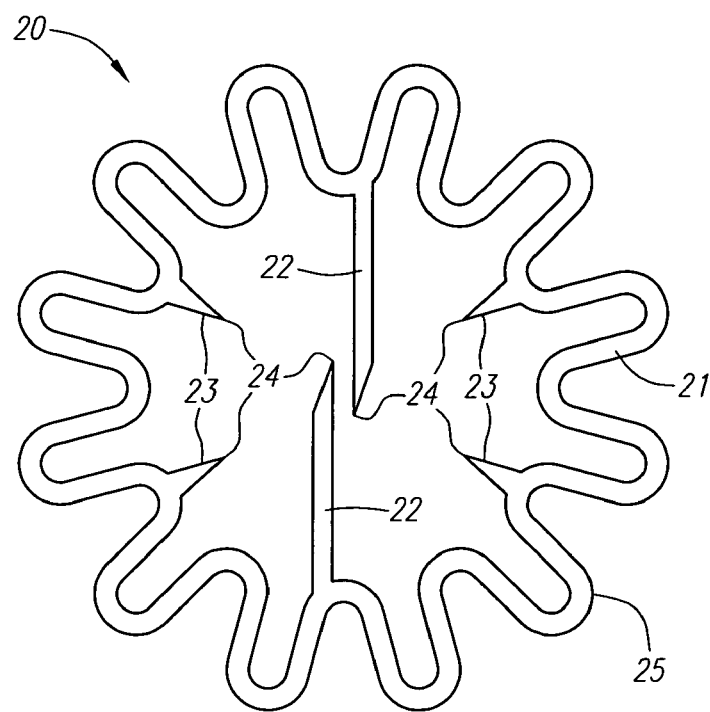
FIGS. 2A AND 2B illustrate the before and after-configuration of a clip manufactured according to another embodiment of the invention.
Figure 2B:
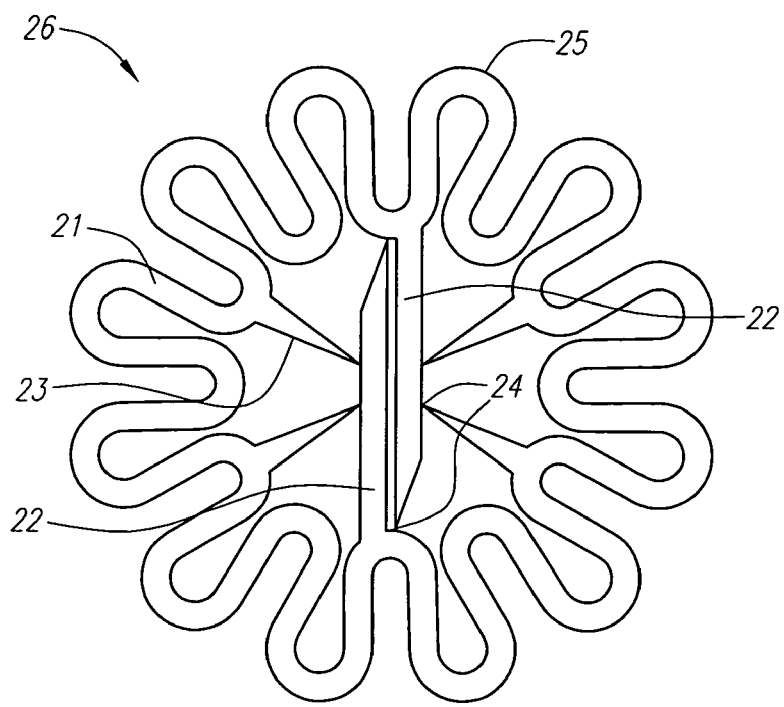

In the alternative embodiment of this invention illustrated in FIGS. 2A and 2B, the precursor 20 is manufactured in an expanded oversize configuration to provide space for removing material from a sheet of material, preferably a superelastic alloy such as nickel-titanium, by conventional methods such as cutting, chemical etching, photochemical etching, stamping, electric discharge machining, laser cutting or the like.

The precursor 20 is reconfigured by imposing radially inwardly directed force on body 21 such that precursor 20 takes a smaller planar shape such as one of those shown in FIG. 2B. The precursor 20 has a planar body 21, tines 22 and 23 having points 24 and such tines are connected by links 25 as previously described with regard to FIG. 1A. The reconfigured precursor is then heat set and quenched as described above to complete the manufacture of clip 26.

Figure 3A:
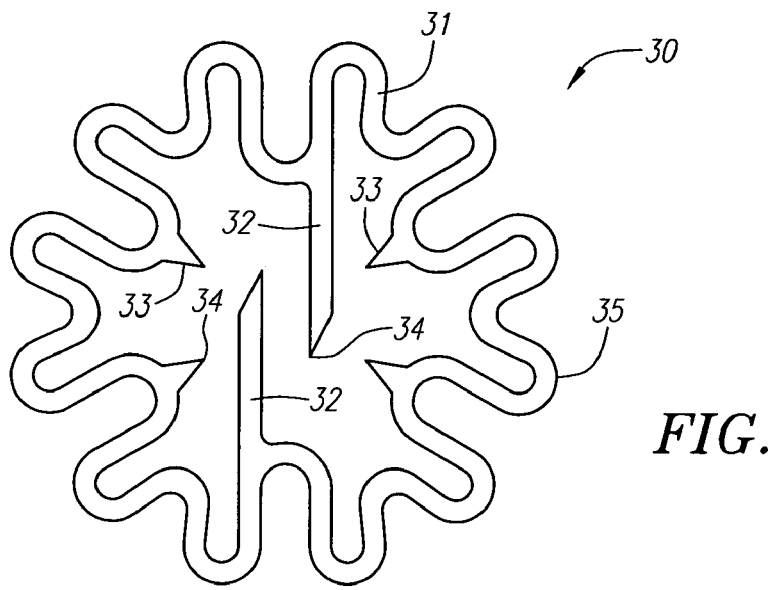
FIGS. 3A–3C illustrate alternate before and after-configurations of clips manufactured according to the method of this invention in which the before configuration is that of FIG. 2A.
Figure 3B:
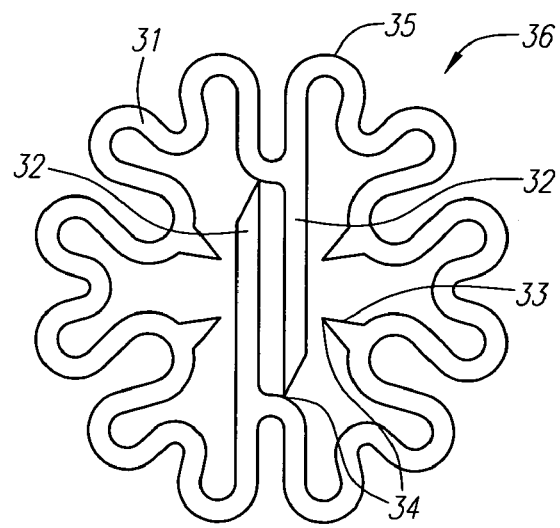
Figure 3C:
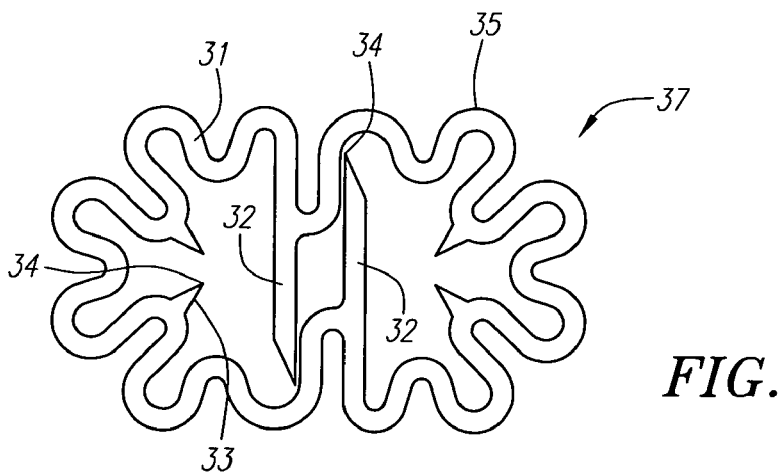

Clips of still other configurations can be manufactured in the manner of clip 26 by starting with a differently shaped precursor such as precursor 30 shown in FIG. 3A. Precursor 30 can be reconfigured by being subjected to radially inward deforming forces as shown in FIG. 3B or by opposed laterally inward forces as shown in FIG. 3C. In each case, the planar body 31 having tines 32 and 33 with points 34 and links 35 will be caused to take a smaller dimension and will be heat set as described above to form clips 36 and 37. Clips manufactured according to the method of the present invention can have a multitude of configurations other than those shown in FIGS. 1B, 2B, and 3C and 3D. For example, the configurations shown in U.S. patent applications Ser. Nos. 09/732,178 and 10/081,726 could be manufactured according to the present invention.

Figure 7:
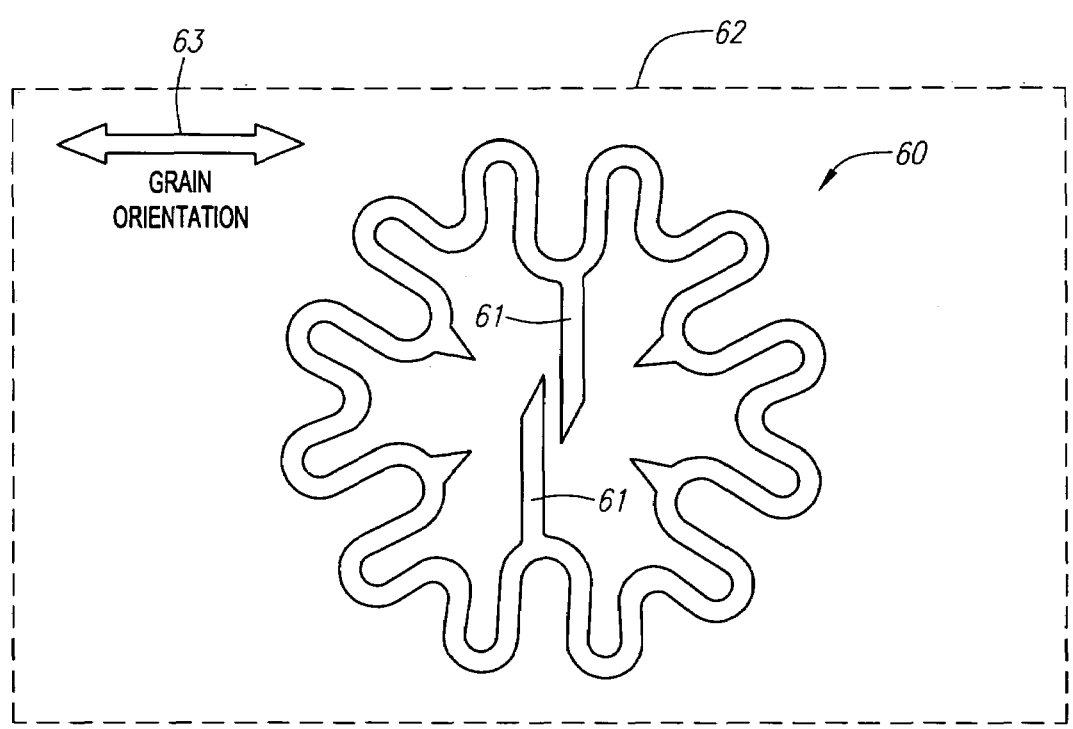
FIG. 7 illustrates the preferred relationship between the grain orientation of a nitinol sheet and the primary tines of a clip precursor.

It has been found that nitinol sheet is stronger in one direction than in others, which may be the result of crystal orientation in the nitinol. It is preferred to form the clip precursors such that the primary tines are aligned with the strongest orientation of the nitinol. It has been found, as shown in FIG. 7, that the greatest strength of the primary tines is achieved if those tines are transverse to the grain orientation of the nitinol. Thus, FIG. 7 illustrates clip precursor 60 having primary tines 61 as the precursor would be cut from sheet 62. The grain orientation of sheet 62 is shown by the double-headed arrow 63. Typically, a plurality of precursors 60 would be cut from the same sheet, each with its primary tines transverse to the grain orientation of the sheet. In addition, even if clips are formed directly without using precursors, it is desirable that their primary tines be transverse to the grain orientation.

Figure 5:
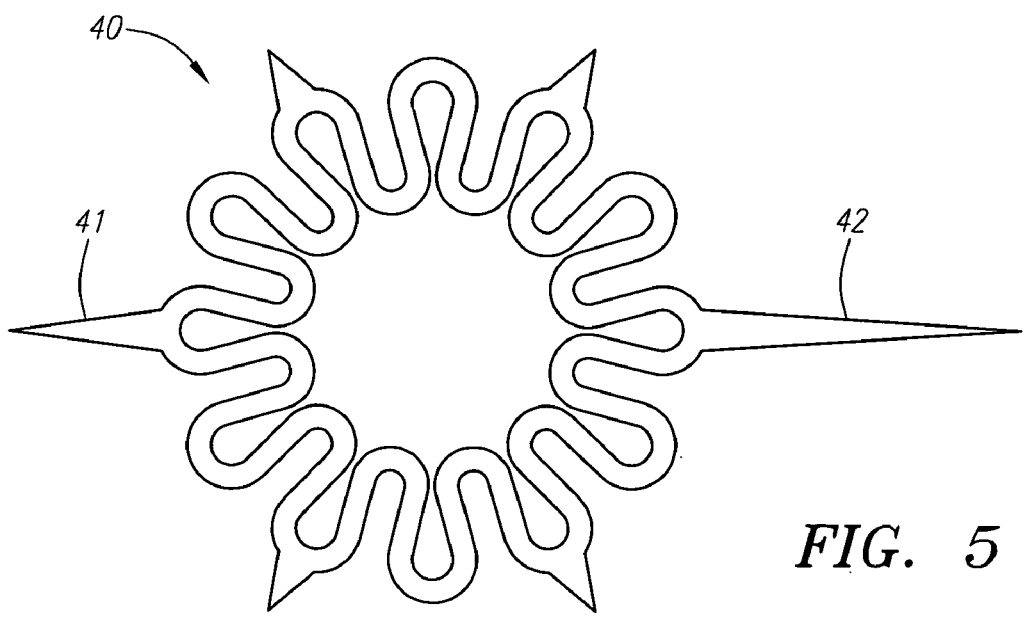
FIGS. 5 and 6 illustrate clip precursors in which radially opposed primary tines have different lengths.
Figure 6:
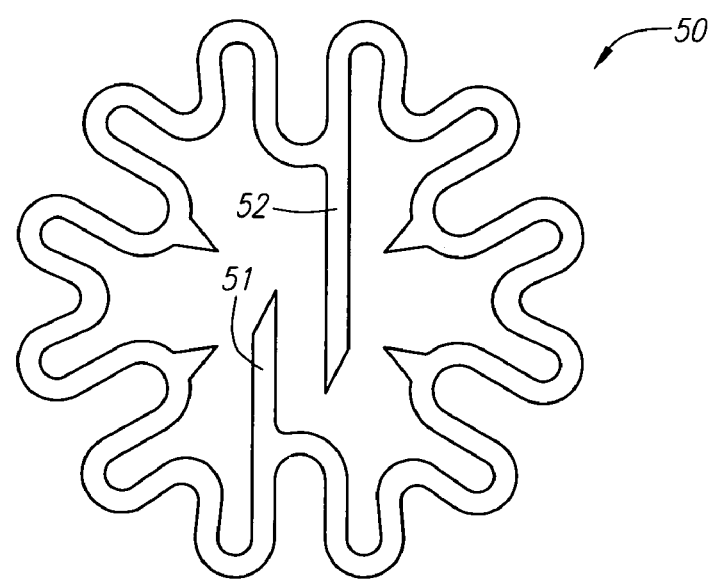

The clips of the present invention may have primary or secondary tines which have the same or different lengths and the tines may be straight or curved. For example, radially opposed tines may have one tine at "12 o'clock" which is longer than the opposing tine at "6 o'clock." Exemplary configurations of clip precursors with primary tines of different length are shown in FIGS. 5 and 6. In FIG. 5, clip precursor 40 is shown with a primary tine 41 which is shorter than primary tine 42. Similarly, in FIG. 6, a clip precursor is shown which has a primary tine 51 which is shorter than primary tine 52.

The clips of the present invention may also be delivered using the apparatus and methods described in U.S. patent application Ser. No. 10/081,273, filed Feb. 21, 2002 which is assigned to the assignee of the present application and the disclosure of which is incorporated by reference herein. Similarly, the apparatus and methods disclosed in U.S. patent application Ser. No. 10/081,717, filed Feb. 21, 2002, which is assigned to the Assignee of the present application and the disclosure of which is incorporated by reference herein, may be used.

Other features can be added to the clips including radio-opaque markers, and/or porous surfaces to promote tissue ingrowth or the clip may be coated in whole or in part with a bioabsorbable material and/or coated with a material containing a substance which is delivered to the patient for therapeutic, diagnostic or other purposes. Such coatings may comprise peptides, clotting factors or other materials designed to benefit the patient.

While the principal object of the present invention is to provide a manufacturing method which facilitates the production of clips having a small footprint, the present invention can also be used to make clips of larger dimensions since, no matter what methods are used to cut the precursor from a sheet of material, the ease of manufacture of even larger size clips is facilitated. Thus, the advantages of the present invention may be realized with regard to clips having larger sizes and clips having a variety of configurations.

Having fully described the present invention including a description of preferred embodiments, it is to be understood that the scope of this invention is not to be limited to those preferred embodiments, but is of the full scope of the appended claims.

What is claimed is:

1. A device for engaging tissue, comprising:

a generally annular-shaped body defining a plane and being disposed about a central axis extending substantially normal to the plane, the body being movable from a first configuration to a second configuration smaller than the first configuration under a radially inwardly directed force and subsequently from a substantially planar configuration lying generally in the plane towards a transverse configuration extending out of the plane, the body comprising a plurality of looped elements comprising alternating first and second curved regions;

at least one first primary tine extending from a first curved region of the annular-shaped body generally towards the central axis in the planar configuration and being deflectable out of the plane when the body is moved towards the transverse configuration, the at least one first primary tine being offset from the axis of symmetry of the first curved region; and at least one second tine extending from the second curved region of the annular-shaped body generally towards the first primary tine when the body is disposed in the planar configuration.

2. The device of claim 1, wherein the body is biased towards the planar configuration for biasing the primary tines generally towards the central axis.

3. The device of claim 1, further comprising:

a set of secondary tines having lengths shorter than the first and second lengths, the secondary tines extending from the annular-shaped body generally towards the central axis in the planar configuration and being deflectable out of the plane when the body is moved towards the transverse configuration.

4. The device of claim 1, wherein the first primary tine, the second primary tine, and the body are formed from a single sheet of material.

5. The device of claim 4, wherein the sheet of material comprises a superelastic alloy.

6. The device of claim 1, wherein the looped elements generally define an endless zigzag pattern extending about the central axis.

7. The device of claim 1, wherein the first primary tine and the second primary tine extend from looped elements disposed opposite one another.

8. The device of claim 7, further comprising a set of secondary tines having lengths shorter than the first and second lengths, the secondary tines extending from the annular-shaped body generally towards the central axis in the planar configuration and being deflectable out of the plane when the body is moved towards the transverse configuration, each pair of adjacent tines having an inner curved region disposed therebetween.

9. The device of claim 8, wherein a secondary tine is disposed on either side of the first primary tine, and a secondary tine is disposed on either side of the second primary tine.

10. The device of claim 1, wherein the plurality of looped elements are expandable between expanded and compressed states for increasing and reducing, respectively, a periphery of the body in the transverse orientation.

11. The device of claim 10, wherein the plurality of looped elements are biased towards the compressed state.

* * * * *

UNITED STATES PATENT AND TRADEMARK OFFICE
CERTIFICATE OF CORRECTION

PATENT NO. : 7,211,101 B2  Page 1 of 1
APPLICATION NO. : 10/335075
DATED : May 1, 2007
INVENTOR(S) : Carley et al.

It is certified that error appears in the above-identified patent and that said Letters Patent is hereby corrected as shown below:

Title Page
Item 56, References Cited, Other Publication, change "Berowe" to --DeRowe--

Column 4
Line 46, change "3C and 3D" to --3B and 3C--

Signed and Sealed this

Eighth Day of July, 2008

JON W. DUDAS
*Director of the United States Patent and Trademark Office*

UNITED STATES PATENT AND TRADEMARK OFFICE
CERTIFICATE OF CORRECTION

PATENT NO. : 7,211,101 B2
APPLICATION NO. : 10/335075
DATED : May 1, 2007
INVENTOR(S) : Michael T. Carley et al.

It is certified that error appears in the above-identified patent and that said Letters Patent is hereby corrected as shown below:

Title Page:

Item 73, Assignee, change "Abbott Vascular Devices" to -- Integrated Vascular Systems, Inc. --

Signed and Sealed this

Twenty-first Day of September, 2010

David J. Kappos
*Director of the United States Patent and Trademark Office*